United States Patent [19]

Niebes et al.

[11] 4,285,964

[45] Aug. 25, 1981

[54] SALTS OF (+)-CATECHINE, THEIR PREPARATION AND USE, AND COMPOSITIONS CONTAINING THESE SALTS

[75] Inventors: Paul Niebes, Grez Doiceau; Andras Vincze, Brussels; Joseph Roba, Ciernont-Houyet; Georges Lambelin, Brussels; Daniel Matagne, Taviers; Etienne Hanon; Michel Franz, both of Brussels, all of Belgium

[73] Assignee: Continental Pharma, Brussels, Belgium

[21] Appl. No.: 71,076

[22] Filed: Aug. 30, 1979

[51] Int. Cl.³ .................... A61K 31/35; C07D 311/62
[52] U.S. Cl. .................................. 424/283; 260/345.2
[58] Field of Search ...................... 260/345.2; 424/283

[56] References Cited

U.S. PATENT DOCUMENTS

| 3,270,003 | 8/1966 | Blaricom et al. | 260/345.2 |
| 4,166,861 | 9/1979 | Bonati et al. | 260/345.2 |

FOREIGN PATENT DOCUMENTS

| 3274 | 11/1978 | European Pat. Off. | 260/345.2 |
| 2128207 | 8/1974 | France | 260/345.2 |

*Primary Examiner*—Nicky Chan
*Attorney, Agent, or Firm*—Cushman, Darby & Cushman

[57] ABSTRACT

A salt of (+)-catechin formed of the reaction product of (+)-catechin with at least a basic amino-acid, such as L-lysine and L-arginine; a hydrosoluble double salt is formed by the reaction product of (+)-catechin with a basic amino-acid, such as L-lysine and L-arginine, and another inorganic or organic acid.

13 Claims, No Drawings

SALTS OF (+)-CATECHINE, THEIR PREPARATION AND USE, AND COMPOSITIONS CONTAINING THESE SALTS

This invention relates to pharmaceutically useful salts of (+)-catechin.

The (+)-catechin is a natural product of the class of flavonoids, having the following formula:

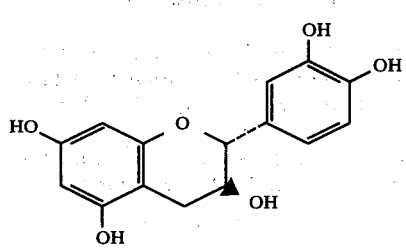

The (+)-catechin [trans-2-(3,4-dihydroxyphenyl)-3,4-dihydro-2H-1-benzopyran-3,5,7-triol] is mainly obtained by extraction of various vegetal species, in particular *Uncaria gambir* (Rubiaceae).

The (+)-catechin has been known for a long time; as early as 1902, the first publications relating to its extraction have appeared. Its chemical structure was determined in 1925 and its stereochemistry in 1955. This substance is presently used as hepato-protecting agent due to its effect on enzymes of the respiratory chain and to its stimulating effect on biosynthesis of ATP.

Use of (+)-catechin in the treatment of degenerative diseases of the connective tissue, such as arthrosis, chondromalacia or parodontosis is a new and original therapeutical use discovered by the inventors and being the subject of another application for patent.

For treating diseases of the articular cartilage, it is important to be able to apply (+)-catechin at the site where it has to be active, namely in the diseased articulation.

It is thus of high interest to have a form of (+)-catechin which may be injected into the articulation. This injectable form must present some essential characteristics such as a good stability and an acceptable local tolerance.

The solubility of (+)-catechin in water (1 g/1100–1200 ml of water) limits its use in specific galenical forms for parenteral administration.

It has been shown that the solubility in water of single or double salts of (+)-catechin is remarkable (up to 400 g/l) and that both of them are directly suitable for preparing pharmaceutical products necessitating a high solubility. This enhanced solubility is of importance for parenteral, oral and topical administration. In certain circumstances it could be useful to prepare pharmaceutical formulations based on double salts, especially for injectable forms.

One of the essential objects of this invention is to provide a salt of (+)-catechin which allows, optionally after a subsequent transformation, its use as an injectable or soluble form having above-mentioned properties.

To this end, according to the invention, the salt consists of the reaction product of (+)-catechin with at least one basic amino-acid.

Advantageously, this salt is a hydrosoluble double salt consisting of the reaction product of (+)-catechin, on one hand, and of a basic amino-acid and another organic or inorganic acid, on the other.

The basic amino-acids used may be natural or not, such as, for example, L-lysine or L-arginine. The solutions of (+)-catechin salts so formed are basic. In order to decrease the pH value to 7.4 (biological pH), it is necessary to add an equivalent amount of another acid. Such an acid may be inorganic, such as, for example, hydrochloric, sulfuric or phosphoric acid, or organic, such as aliphatic, cycloaliphatic, aromatic, araliphatic or heterocyclic, carboxylic or sulfonic acids, for example acetic, propionic, succinic, glycolic, gluconic, lactic, malic, tartaric, citric, ascorbic, glucuronic, maleic, fumaric, pyruvic, aspartic, glutamic, mandelic, methanesulfonic, ethanesulfonic, panthotenic, β-hydroxypropionic, β-hydroxybutyric, malonic, galactaric and galacturonic acids.

Thus, to a solution comprised of one mole of (+)-catechin and one mole of L-lysine or L-arginine, it is necessary to add, for example, one mole of hydrochloric, acetic, ascorbic or glucuronic acid or instead of the latter one third of one mole of phosphoric or nitric acid.

The preferred double salts according to this invention consist of (+)-catechin, L-lysine and hydrochloric or ascorbic acid.

In general, the solutions of double salts of (+)-catechin formed with 1 equivalent of basic amino-acid and 1 equivalent of acid present a pH around 7.4.

These double salts of (+)-catechin are all hydrosoluble but the solubility varies somewhat as a function of the acid used. Thus the solubility of salts formed with L-lysine and with ascorbic, hydrochloric, acetic and glucuronic acids, in the presence of 2% of benzyl alcohol is above 15 mg of (+)-catechin per ml (which approximately corresponds to an isotonic concentration), while the solubility of the same salt formed with citric acid is 9.5 mg of (+)-catechin per ml.

This invention also relates to the preparation of these double salts.

According to the first way of proceeding, (+)-catechin is added to an aqueous solution containing the basic amino-acid and the acid in suitable amounts. The mixture is then brought to such a temperature that it prevents isomerization of (+)-catechin. This temperature is advantageously between 30° and 65° C., preferably about 45° C., until a clear solution is obtained.

Another way of proceeding consists of bringing up to a temperature between 30° and 60° C., advantageously about 45° C., an aqueous solution of the basic amino-acid salt and slowly dissolving therein the suitable amount of (+)-catechin.

In both cases, the pH is adjusted to an acceptable value by adding a suitable amino-acid as free base, or an acid as the case may require.

Upon cooling, salts precipitate and 1 to 3% of benzyl alcohol are added, advantageously 2%. The solution is reheated to about 45° C. and allowed to cool again, preferably to below 10° C. The double salt then remains in solution.

In order to obtain a powder, the solvent may then be removed by moderate heating under vacuum or by lyophilization. A water soluble powder is so obtained, which may be used for preparing solid forms (tablets, suppositories, lozenges, granules, dragees, film coated tablets . . . ) semi-solid forms (unguents, creams, gells, pastes . . . ) and liquid forms (suspensions, sirops, drops, solutions . . . ). It is obvious that the solutions of double salts of (+)-catechin, prepared as hereinafter explained, may be used immediately as injectable products without being previously lyophilized.

Hereinafter some non limitative examples for preparing compounds according to the invention are given.

EXAMPLE 1

22.6 g (0.155 mole) of L-lysine are dissolved in 400 ml of distilled and deoxygenated water heated to 40° C. and 45 g (0.155 mole) of (+)-catechin are added. The mixture is stirred until complete dissolution.

The slightly colored solution is diluted to 1000 ml and filtered on Millipore 0.22 μm under sterile conditions.

The solutions are lyophilized until the residual humidity is less than 1%. This powder may be used for the preparation of solid, semi-solid and liquid galenical forms.

For parenteral use, 1 ml of the solution of catechin lysinate prepared as hereinabove mentioned is added in sterilized vials having a useful capacity of 3 ml.

The vials are sealed under nitrogen. The lyophilized product is sterile. The preparation of an injectable form of double salt is carried out extemporaneously by dissolving the vial content into 3 ml of the following sterile acid solution:

Ascorbic acid: 25.7 mg
Anhydrous glucose: 18.0 mg
Benzyl alcohol: 45.0 mg
Distilled water for injection ad: 3 ml

EXAMPLE 2

7.55 g (0.053 mole) of L-lysine are dissolved in 800 ml of distilled and deoxygenated water heated to 40° C. and 15 g (0.052 mole) of (+)-catechin are added. The mixture is stirred until complete dissolution.

After cooling to room temperature, about 50 ml of 1 N hydrochloric acid solution are added to obtain a pH of 7.4.

This solution is kept under nitrogen for 24 hours at a temperature lower than 10° C.

The precipitate which appears must be eliminated by heating to 40° C.

Then, 20 g of benzyl alcohol are added and after cooling to room temperature, the volume is brought to 1 liter with bidistilled and deoxygenated water.

After filtration under proper conditions, the solution is divided and poured into brown vials of 1 ml content.

EXAMPLE 3

7.55 g (0.053 mole) of L-lysine are dissolved in 800 ml of distilled and deoxygenated water heated to 40° C., and 15 g (0.052 mole) of (+)-catechin are added. One stirs till complete dissolution.

After cooling to room temperature, a solution containing 9.1 g of ascorbic acid is added. The pH is adjusted to 7.4 with the necessary amount of amino-acid or ascorbic acid.

This solution is kept under nitrogen for 24 hours at a temperature lower than 10° C.

The precipitate which appears must be eliminated by heating to 40° C.

Then 20 g of benzyl alcohol are added and after cooling to room temperature, the volume is brought to 1 liter with bidistilled and deoxygenated water.

After filtration under proper conditions, the solution is divided and poured into brown vials of 1 ml content.

EXAMPLE 4

9.25 g (0.05 mole) of L-lysine monohydrochloride are dissolved in 700 ml of distilled and deoxygenated water heated to 40° C. 15 g (0.052 mole) of (+)-catechin are added and stirred until complete dissolution.

After cooling, the pH is adjusted to 7.2 with lysine (free base). The solution is then kept under nitrogen for 24 hours at a temperature lower than 10° C.

The precipitate which appears must be eliminated by heating to 40° C.

Then 20 g of benzyl alcohol are added and after cooling to room temperature, the solution is brought to a volume of 1 liter with bidistilled and deoxygenated water.

After filtration under suitable conditions, the solution is divided and poured into brown vials of 1 ml content.

EXAMPLE 5

9.0 g (0.052 mole) of L-arginine monohydrochloride are dissolved in 700 ml of distilled and deoxygenated water heated to 40° C. 15 g (0.052 mole) of (+)-catechin are added and the mixture is stirred until complete dissolution.

After cooling, the pH is adjusted to 7.2 with arginine (free base).

This solution is kept under nitrogen for 24 hours at a temperature lower than 10° C.

The precipitate which forms must be eliminated by heating to 40° C.

Then 20 g of benzyl alcohol are added and after cooling to room temperature, the volume is brought to 1 liter with bidistilled and deoxygenated water.

After filtration under suitable conditions, the solution is divided and poured into brown vials of ml content.

EXAMPLE 6

17.6 g (0.1 mole) of ascorbic acid are dissolved in 200 ml of distilled and deoxygenated water. An equimolar amount of L-lysine is added and the mixture is stirred until complete dissolution.

29 g (0.1 mole) of (+)-catechin are then added and the mixture is heated at a temperature of 60° C.

After complete dissolution, the product is evaporated to dryness under vacuum in a exsiccator containing phosphorus hemipentoxide.

The dry product is passed through a sieve of 1 mm and, if necessary dried again to obtain a residual humidity less than 1%.

These operations are to be conducted in the absence of oxygen and light.

A crystalline powder of a brownish color and of a melting point between 125° and 127° C. is obtained. The water solubility is 40 g/l; the pH of an aqueous concentrated solution is 6.5.

EXAMPLE 7

The powder obtained according to the method described in the preceeding example may be used for preparing solid formulations.

E.g., a tablet of the following formula has been prepared:

| | |
|---|---|
| (+)-catechin | 527 mg. |
| Special hot soluble starch | 53 mg. |
| Microcrystalline cellulose | 67 mg. |
| Magnesium stearate | 3 mg. |

EXAMPLE 8

The powder obtained according to the method described in Example 6 may be used for preparing suppositories. The following formula has been used.

| (+)-catechin hydrochlorolysinate | 843 mg. |
|---|---|
| Witepsol H 35 | 2.157 mg. |
| Total weight | 3.000 mg. |

The local tolerance to intra-articular injection of compounds according to the invention has been tested in dogs at the daily dose of 0.5 ml of a 15 mg/ml solution, five days a week for 3 weeks. No intolerance phenomena whether local or general, have been evidenced.

The double salts based on (+)-catechin exert a fundamental protecting action on the connective tissue against degeneration spontaneous or consecutive to chronical inflammatory processes.

The recommended doses for the preferred modes of administration are 1 to 4 g, advantageously 2 to 3 g per day, orally or rectally and 5 to 50 mg per day intravenously or intra-articularly.

If topically applied, the recommended doses are of about 100 mg to 2 g for each application.

The salts of (+)-catechin may be administered in association with various pharmaceutical excipients, orally, parenterally, rectally, topically, and intra-articularly.

For oral administration, dragees, granules, lozenges, capsules, tablets, film coated tablets, solutions, syrups, emulsions are prepared with additives or excipients commonly used in galenical pharmacy. These galenical forms may release the active agent in a normal or a time-programmed way.

For parenteral or intra-articular administration, the salt may be dissolved in a suitable aqueous solution.

For rectal administration, suppositories and rectal capsules will be used.

For topical administration, creams, pastes, gels and ointments will be prepared.

The active compound may be employed alone or in combination with other active products having a similar or different activity.

The following indicative example illustrates the method for extracting (+)-catechin used within the scope of this invention.

In a reactor, 23.9 kg of Block Gambir and 190 l of ethyl acetate (AcOEt) were heated at 65°–70° C. for 1 hour. Then 1.5 kg of animal charcoal were added and stirred for 1 hour at 65°–70° C. The solution so obtained was filtered through "Nutsche" with a Celite bed (2 kg of Celite) and the cake washed with 2×20 l of AcOEt. The filtrate was concentrated by heating under vacuum (59°–73° C./70 mml Hg). 148 l of permutated water were added and AcOEt was eliminated by azeotropic distillation with return of water into the reactor. 1.26 kg of animal charcoal were added to the aqueous solution which was then heated, stirred and hot filtered on a Büchner filter. The filtrate was cooled to 5° C. under nitrogen.

The (+)-catechin was precipitated as a yellowish powder, filtered through "Nutsche" and washed with iced permutated water. The cake was centrifuged and the product dried under vacuum at ±35° C.

The weight of (+)-catechin so obtained was 8.5 kg with a humidity of ±15% (yield with respect to Block Gambir: 35.55%). The (+)-catechin was identified by infrared spectrometry and the water content was determined by the Karl-Fisher method.

We claim:

1. A salt of (+)-catechin which is the reaction product of (+)-catechin with at least one basic amino-acid selected from the group consisting of L-lysine and L-arginine.

2. A hydrosoluble double salt of (+)-catechin which is the reaction product of (+)-catechin, a basic amino-acid selected from the group consisting of L-lysine and L-arginine and another acid selected from the group consisting of hydrochloric acid, ascorbic acid, acetic acid and citric acid.

3. A salt as claimed in claim 2, wherein the basic amino-acid is L-lysine and said other acid is hydrochloric acid.

4. A salt as claimed in claim 2, wherein the basic amino-acid is L-lysine and said other acid is ascorbic acid.

5. A salt as claimed in claim 2 wherein said (+)-catechin, said basic amino-acid and said other acid are present in substantially equivalent amounts.

6. A pharmaceutical composition for the treatment of diseases of the articular cartilage comprising, as active product, an effective amount of at least one hydrosoluble double salt of (+)-catechin as claimed in claim 2, in association with a suitable excipient.

7. An orally, topically, rectally or parenterally administerable pharmaceutical composition for the treatment of diseases of the articular cartilage comprising, as active product, an effective amount of at least one hydrosoluble salt of (+)-catechin as claimed in claim 1, in association with a suitable excipient.

8. A method for treating degenerative diseases of the connective tissue, which comprises administering a salt of (+)-catechin as claimed in claim 1 orally or rectally at a daily dosage of 1 to 4 g or intravenously or intra-articularly at a daily dosage of 5 to 50 mg.

9. A method for treating degenerative diseases of the connective tissue, which comprises administering a double salt of (+)-catechin as claimed in claim 2 orally or rectally at a daily dosage of 1 to 4 g or intravenously or intra-articularly at a daily dosage of 5 to 50 mg.

10. A method for treating degenerative diseases of the connective tissue which comprises topically administering a salt of (+)-catechin as claimed in claim 1 in an amount of 100 mg to 2 g.

11. The method of claim 8 wherein said salt of (+)-catechin is in the form of an orally, topically, rectally or parenterally administerable composition comprising, as active product, an effective amount of at least one hydrosoluble salt of (+)-catechin which is the reaction product of (+)-catechin with at least one basic amino-acid selected from the group consisting of L-lysine and L-arginine in association with a suitable excipient.

12. The method of claim 9 wherein said salt of (+)-catechin is in the form of a composition comprising, as active product, an effective amount of at least one hydrosoluble double salt of (+)-catechin which is the reaction product of (+)-catechin, a basic amino-acid selected from the group consisting of L-lysine and L-arginine and another acid selected from the group consisting of hydrochloric acid, ascorbic acid, acetic acid and citric acid, in association with a suitable excipient.

13. The method of claim 10 wherein said salt of (+)-catechin is in the form of an orally, topically, rectally or parenterally administerable composition comprising, as active product, an effective amount of at least one hydrosoluble salt of (+)-catechin which is the reaction product of (+)-catechin with at least one basic amino-acid selected from the group consisting of L-lysine and L-arginine in association with a suitable excipient.

* * * * *